US008710282B2

(12) United States Patent
Bektesevic et al.

(10) Patent No.: US 8,710,282 B2
(45) Date of Patent: Apr. 29, 2014

(54) INTEGRATED PROCESS FOR THE MANUFACTURE OF FLUORINATED OLEFINS

(75) Inventors: Selma Bektesevic, Williamsville, NY (US); Hsueh Sung Tung, Getzville, NY (US); Haluk Kopkalli, Staten Island, NY (US)

(73) Assignee: Honeywell International Inc., Morristown, NJ (US)

( * ) Notice: Subject to any disclaimer, the term of this patent is extended or adjusted under 35 U.S.C. 154(b) by 19 days.

(21) Appl. No.: 13/229,016

(22) Filed: Sep. 9, 2011

(65) Prior Publication Data

US 2012/0022302 A1 Jan. 26, 2012

Related U.S. Application Data

(63) Continuation-in-part of application No. 13/195,429, filed on Aug. 1, 2011, now Pat. No. 8,242,316, which is a continuation-in-part of application No. 12/402,372, filed on Mar. 11, 2009, now Pat. No. 8,013,194.

(60) Provisional application No. 61/392,242, filed on Oct. 12, 2010, provisional application No. 61/036,526, filed on Mar. 14, 2008.

(51) Int. Cl.
*C07C 17/25* (2006.01)
*C07C 19/08* (2006.01)
*C07C 21/18* (2006.01)

(52) U.S. Cl.
USPC .......................................... 570/157; 570/155

(58) Field of Classification Search
None
See application file for complete search history.

(56) References Cited

U.S. PATENT DOCUMENTS

| | | | |
|---|---|---|---|
| 4,876,405 A | 10/1989 | Gervasutti | |
| 5,396,000 A | 3/1995 | Nappa et al. | |
| 5,672,787 A | 9/1997 | Bielefeldt et al. | |
| 5,672,803 A | 9/1997 | Smith et al. | |
| 5,679,875 A | 10/1997 | Aoyama et al. | |
| 5,714,655 A | 2/1998 | Yamamoto et al. | |
| 6,031,141 A | 2/2000 | Mallikarjuna et al. | |
| 6,369,284 B1 | 4/2002 | Nappa et al. | |
| 6,548,719 B1 | 4/2003 | Nair et al. | |
| 6,734,332 B1 | 5/2004 | Slaugh et al. | |
| 7,230,146 B2 | 6/2007 | Merkel et al. | |
| 7,560,602 B2 | 7/2009 | Van Der Puy et al. | |
| 2004/0119047 A1 | 6/2004 | Singh et al. | |
| 2006/0106263 A1 | 5/2006 | Miller et al. | |
| 2007/0123741 A1 | 5/2007 | Van Der Puy et al. | |
| 2007/0129579 A1 | 6/2007 | Wang et al. | |
| 2009/0234165 A1 | 9/2009 | Chiu et al. | |
| 2009/0278075 A1 | 11/2009 | Mahler et al. | |
| 2010/0029997 A1 | 2/2010 | Wang et al. | |
| 2010/0145111 A1 | 6/2010 | Sharratt et al. | |
| 2010/0305370 A1 | 12/2010 | Devic et al. | |
| 2011/0021849 A1 | 1/2011 | Avril et al. | |
| 2011/0112338 A1 | 5/2011 | Smith et al. | |
| 2011/0190554 A1 | 8/2011 | Pigamo et al. | |

FOREIGN PATENT DOCUMENTS

| | | |
|---|---|---|
| CA | 2152031 A1 | 12/1995 |
| EP | 0442087 A1 | 8/1991 |
| EP | 0644173 A1 | 3/1995 |
| EP | 0688751 A1 | 12/1995 |
| EP | 0726243 A1 | 8/1996 |
| EP | 0982281 A1 | 3/2000 |
| FR | 2935702 A1 | 3/2010 |
| JP | 08165256 A | 6/1996 |
| WO | 9833755 A1 | 8/1998 |
| WO | 2007/117391 A1 | 10/2007 |
| WO | 2009/084703 A1 | 7/2009 |
| WO | 2009/125201 A2 | 10/2009 |
| WO | 2010029239 A1 | 3/2010 |
| WO | 2010139873 A1 | 12/2010 |
| WO | 2011010024 A1 | 1/2011 |

OTHER PUBLICATIONS

Meriam-Webster online dictionary, retrieved on Aug. 26, 2009. http://www.merriam-webstercom/dictionary/stage US.
Knunyants, et al., "Reactions of Fluoro Olefins Communication 13. Catalytic Hydrogenation of Perfluoro Olefins," 1960, Bulletin of the Academy of Sciences of the USSR, Division of Chemical Sciences, pp. 1312-1317 (XP000578879) USSR.
Kiyoshi Endo et al., "Monomer-Isomerization Polymerization-XXVI. The Case of 2-Butene in the Presence of Isobutene with Ziegler-Natta Catalyst," Eur. Polym. J., vol. 28, No. 2, pp. 153-157 (1992).
PCT/US/2011/55198 Search Report, dated May 4, 2012.

*Primary Examiner* — Clinton Brooks
(74) *Attorney, Agent, or Firm* — Bruce O. Bradford

(57) ABSTRACT

The instant invention relates, at least in part, to a method increasing the cost efficiency for dehydrohalogenation production of a fluorinated olefin by recovering and recycling spent dehydrohalogenation agent. In one aspect, the present invention relates to dehydrohalogenating a fluorinated alkane (e.g. pentafluoropropane and/or hexafluoropropane) in the presence of a dehydrohalogenating agent to produce a fluorinated olefin (e.g. tetrafluoropropenes and/or pentafluoropropenes). Removal of spent dehydrohalogenating agent from the reactor allows for facile separation of organic and dehydrohalogenating agent, the latter of which is recycled.

46 Claims, 3 Drawing Sheets

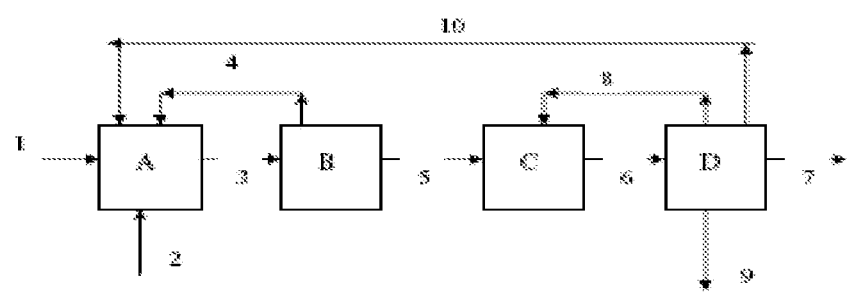
FIGURE 1
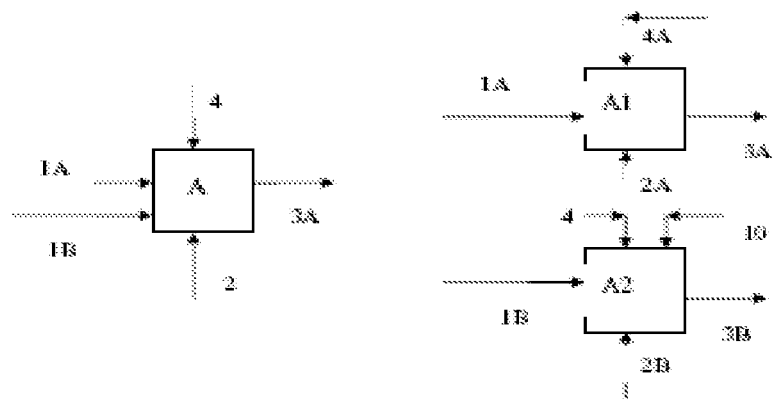
FIGURE 2
FIGURE 3

INTEGRATED PROCESS FOR THE MANUFACTURE OF FLUORINATED OLEFINS

CROSS-REFERENCE TO RELATED APPLICATIONS

This application is related to and claims the priority benefit of U.S. provisional application No. 61/392,242, filed Oct. 12, 2010, the contents of which are incorporated herein by reference.

This application is also a continuation-in-part of U.S. application Ser. No. 13/195,429, filed Aug. 1, 2011 (now U.S. Pat. No. 8,242,316), which is a continuation of U.S. patent application Ser. No. 12/402,372, filed Mar. 11, 2009 (now U.S. Pat. No. 8,013,194), which in turn claims priority benefit of U.S. Provisional Patent Application No. 61/036,526, filed Mar. 14, 2008, each of which is incorporated herein by reference.

FIELD OF THE INVENTION

The present invention relates to processes for producing haloalkenes, particularly, though not exclusively, 2,3,3,3-tetrafluoropropane (HFO-1234yf) and/or 1,2,3,3,3-pentafluoropropene (HFO-1225ye).

BACKGROUND OF THE INVENTION

Chlorine-containing compounds, such as chlorofluorocarbons (CFCs), have been employed as refrigerants, foam blowing agents, cleaning agents, solvents, heat transfer media, sterilants, aerosol propellants, dielectrics, fire extinguishing agents, and power cycle working fluids. Such chlorine-containing compounds have proven to be detrimental to the Earth's ozone layer. Many of the hydrofluorocarbons (HFCs), used as the substitutes of CFCs, have been found to contribute to global warming. For these reasons, there is a worldwide effort to develop new compounds that are more environmentally benign while at the same time being as effective, or more effective, from a performance standpoint.

Applicants have come to appreciate that 1,2,3,3,3-pentafluoropropene (HFO-1225ye) and 2,3,3,3-tetrafluoropropene (HFO-1234yf) are each useful in one or more of the above mentioned applications. Accordingly, compositions containing either or both fluorinated olefins are among the materials being developed for such use.

Methods for producing HFO-1234yf and HFO-1225ye are known. In one example, it is known that hexafluoropropylene (HFP) can be hydrogenated to produce 1,1,1,2,3,3-hexafluoropropane (HFC-236ea). HFC-236ea is then used as a reactant in a dehydrogenation reaction to produce HFO-1225ye. It is further known that HFO-1225ye can be hydrogenated to produce 1,1,1,2,3-pentafluoropropane (HFC-245eb) and that HFC-245eb can then be dehydrofluorinated to produce HFO-1234yf.

U.S. Patent Application Publication No. 2009/0234165, the contents of which are incorporated by reference herein, further provides that HFO-1225ye and HFO-1234yf can be produced in a single facility. Most notably, it was realized that the hydrogenation of HFP can yield both HFC-236ea and HFC-245eb and that these two products can be simultaneously dehydrofluorinated to produce HFO-1225ye and HFO-1234yf, respectively. Processing conditions are taught to be adjustable, so as to favor the selective conversion of one hydrofluoroolefin over the other. Catalysts that may be used for such reactions were taught to include metal catalysts, even more preferably one or more transition metal-based catalysts (including in certain preferred embodiments transition metal halide catalysts), such as $FeCl_3$, chromiumoxyfluoride, Ni (including Ni mesh), $NiCl_2$, $CrF_3$, and mixtures thereof, supported or in bulk. Other catalysts include carbon-supported catalysts, antimony-based catalysts (such as $SbCl_5$), aluminum-based catalyst (such as $AlF_3$, $Al_2O_3$, and fluorinated $Al_2O_3$), palladium-based catalysts, platinum-based catalysts, rhodium-based catalysts and ruthenium-based catalysts, including combinations thereof.

Other examples of methods for the production of HFO-1225ye and HFO-1234yf are set forth in, at least, U.S. Pat. No. 7,560,602, which is assigned to the assignee of the present invention and is incorporated herein by reference. This patent discloses a similar dehydrohalogenation process for producing 2,3,3,3-tetrafluoropropene (1234yf) and 1,2,3,3,3-pentafluoropropene (HFO-1225ye) by catalytic dehydrofluorination of 1,1,1,2,3-pentafluoropropane (245eb) and 1,1,1,2,3,3-hexafluoropropane (HFC-236ea), respectively. Preferred dehydrohalogenation catalysts include fluorinated chromium oxide catalysts, aluminum fluoride catalysts, ferric fluoride catalysts, mixtures of magnesium fluoride and aluminum fluoride catalysts, nickel-based catalysts, carbon based catalysts, and combinations thereof.

Alternative agents for such dehydrohalogenation reactions are also known. U.S. Patent Application Publication No. 20100029997, for example, teaches the production of hydroolefins (e.g. HFO-1234yf) by dehydrohalogenating HFC-245eb by contacting it to potassium hydroxide (KOH), sodium hydroxide (NaOH), $Ca(OH)_2$, CaO, and combinations thereof. While, in certain embodiments, dehydrohalogenation agents include KOH, alternative agents also include LiOH, $Mg(OH)_2$ and NaOH.

Applicants have come to appreciate that during continuous processing using such dehydrohalogenation agents (also referred to as "reagent"), the reaction proceeds until either the organic reactants or dehydrohalogenation agent is consumed. Upon completion of the reaction, the reactor must be dismantled to remove the salt and/or salt solutions. This, in turn creates higher operating costs and reduces productivity. Accordingly, more efficient process is desirable for removal of spent reagent and recycle of unused or regenerated reagent and/or unused organics during a continuous process.

Applicants assert that the instant invention addresses the foregoing needs.

SUMMARY OF THE INVENTION

The instant invention relates, at least in part, to a method of increasing the cost efficiency for dehydrohalogenation production of a fluorinated olefin by recovering and recycling spent reagent. In one aspect, the present invention relates to dehydrohalogenating a fluorinated alkane (e.g. pentafluoropropanes and/or hexafluoropropanes) in the presence of a dehydrohalogenating agent to produce a fluorinated olefin (e.g. tetrafluoropropenes and/or pentafluoropropenes). Such dehydrohalogenating agents may include, but are not limited to, potassium hydroxide (KOH), sodium hydroxide (NaOH), calcium hydroxide ($Ca(OH)_2$), lithium hydroxide (LiOH), magnesium hydroxide ($Mg(OH)_2$), calcium oxide (CaO), or combinations thereof. Removal of spent dehydrohalogenating agent from the reactor allows for facile separation of the organic and the dehydrohalogenating agent. This in turn leads to lower cost associated with design and operation of complicated and highly specialized separation equipment. Recycling the spent dehydrohalogenating agent leads to greater efficiency. Increased productivity is similarly observed if metal fluoride salts are also isolated from the product stream, converted back to the dehydrohalogenating agent's original form, and recycled to the reaction.

In one aspect, the instant invention relates to a method or process for manufacturing a fluoroolefin including: (a) hydrogenating a first haloolefin to produce a haloalkane; (b) optionally separating said haloalkane into a plurality of intermediate product streams comprising two or more streams selected from the group consisting of a first rich in at least a first alkane, a second stream rich in a second alkane and an alkane recycle stream; (c) dehydrohalogenating the haloalkane in (a) or (b) in the presence of a dehydrohalogenating agent to produce a second haloolefin; (d) withdrawing a reaction stream comprising spent dehydrohalogenating agent and, optionally, metal fluoride salt by products; and (d) recovering, purifying and/or regenerating spent dehydrohalogenating agent. The first haloolefin may include a compound of formula (I)

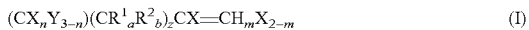
$$(CX_nY_{3-n})(CR^1{}_aR^2{}_b)_zCX=CH_mX_{2-m} \qquad (I)$$

wherein each X is independently Cl, F, I or Br, provided that at least two Xs are F; each Y is independently H, Cl, F, I or Br; each $R^1$ is independently H, Cl, F, I, Br or unsubstituted or halogen substituted methyl or ethyl radical; each $R_2$ is independently H, Cl, F, I, Br or unsubstituted or halogen substituted methyl or ethyl radical; n is 1, 2 or 3; a and b are each 0, 1 or 2, provided that a+b=2; m is 0, 1 or 2; and z is 0, 1, 2 or 3.

In further embodiments of the foregoing, the first haloolefin is comprised of a compound of formula (IA)

$$CX_nY_{3-n}CX=CH_mX_{2-m} \qquad (IA)$$

wherein each X is independently Cl, F, I or Br, provided that at least two Xs are F; each Y is independently H, Cl, F, I or Br; n is 1, 2 or 3; and m is 0, 1 or 2.

In even further embodiments of the foregoing, the first haloalkane is hexafluoropropylene (HFP).

The first haloalkane of the reaction process may be, in certain embodiments, any compound of formula (II)

$$(CX_nY_{3-n})(CR^1{}_aR^2{}_b)_zCHXCH_{m+1}X_{2-m} \qquad (II)$$

wherein each X is independently Cl, F, I or Br, provided that at least two Xs are F; each Y is independently H, Cl, F, I or Br; each $R^1$ is independently H, Cl, F, I, Br or unsubstituted or halogen substituted methyl or ethyl radical; each $R_2$ is independently H, Cl, F, I, Br or unsubstituted or halogen substituted methyl or ethyl radical; n is 1, 2 or 3; a and b are each 0, 1 or 2, provided that a+b=2; m is 0, 1 or 2; and z is 0, 1, 2 or 3.

In further embodiments of the foregoing, the haloalkane is a compound of formula (IIA):

$$(CX_nY_{3-n})CHXCH_{m+1}X_{2-m} \qquad (IIA)$$

wherein each X is independently Cl, F, I or Br, provided that at least two Xs are F; each Y is independently H, Cl, F, I or Br; n is 1, 2 or 3; and m is 0, 1 or 2.

In even further embodiments of the foregoing, the intermediate haloalkane is 1,1,1,2,3,3-hexafluoropropane (HFC-236ea) and/or 1,1,1,2,3-pentafluoropropane (HFC-245eb).

The second haloolefin may be, in certain embodiments, any compound of the formula (III):

$$(CX_nY_{3-n})(CR^1{}_aR^2{}_b)_ZCX=CH_{m+1}X_{1-m} \qquad (III)$$

wherein each X is independently Cl, F, I or Br, provided that at least two Xs are F; each Y is independently H, Cl, F, I or Br; each $R^1$ is independently H, Cl, F, I, Br or unsubstituted or halogen substituted methyl or ethyl radical; each $R_2$ is independently H, Cl, F, I, Br or unsubstituted or halogen substituted methyl or ethyl radical; n is 1, 2 or 3; a and b are each 0, 1 or 2, provided that a+b=2; m is 0 or 1; and z is 0, 1, 2 or 3.

In further embodiments of the foregoing, the second haloolefin is comprised of a compound of the formula (IIIA):

$$(CX_nY_{3-n})CX=CH_{m+1}X_{1-m} \qquad (IIIA)$$

wherein each X is independently Cl, F, I or Br, provided that at least two Xs are F; each Y is independently H, Cl, F, I or Br; n is 1, 2 or 3; and m is 0 or 1.

In even further embodiments of the foregoing, the second haloolefin is 2,3,3,3-tetrafluoropropene (1234yf) and/or 1,2,3,3,3-pentafluoropropene (HFO-1225ye).

In embodiments where the second haloolefin is HFO-1225ye and/or HFO-1234yf, for example, the foregoing reactions can be produced in a single facility having four unit operations. More specifically, hydrogenation of HFP with hydrogen is known to yield both HFC-236ea and HFC-245eb. Like HFC-236ea, HFC-245eb subsequently can be dehydrofluorinated to produce a desirable product. In particular, HFC-236ea can be dehydrofluorinated to produce HFO-1225ye and HFC-245eb can be dehydrofluorinated to produce HFO-1234yf. Thus, both HFO-1225ye and HFO-1234yf can be produced using a single set of four unit operations: hydrogenation of the starting material, separation of the desired intermediate, dehydrofluorination of the intermediate to produce the desired product, followed by another separation to isolate the desired product. For example, in a one system, HFP and $H_2$ are reacted in a hydrogenation reactor to form an intermediate product stream comprising HFC-236ea and/or HFC-245eb. The relative concentrations of HFC-236ea and HFC-245eb is dependant on reaction conditions in the hydrogenation reactor, such as pressure, temperature, and relative concentration of reactants in the reactor. If the desirable end product is HFO-1225ye, then processing conditions preferably favor the production of HFC-236ea. That is, the hydrogenation reactor is operated to produce an intermediate product stream rich in HFC-236ea which is subsequently separated from the intermediate process stream and fed into a dehydrofluorination reactor to form a final product stream comprising HFO-1225ye. This HFO-1225ye is then separated from the final product stream and recovered as a purified product. If the desirable end product is HFO-1234yf, then processing conditions preferably favor the production of HFC-245eb. That is, the hydrogenation reactor is operated to produce an intermediate product stream rich in HFC-245eb. This can be accomplished by operating the hydrogenation reactor under conditions favorable to convert the HFP into HFC-236ea and then converting the HFC-236ea into HFC-245eb. The HFC-245eb is then separated from the intermediate product stream and fed into a dehydrofluorination reactor to form a final product stream comprising HFO-1234yf. This HFO-1234yf is then separated from the final product stream and recovered as a purified product.

In addition, when HFO-1234yf is the desired product, HFO-1225ye can be introduced into the hydrogenation reactor at some point and then converted into HFC-245eb. The source of this HFO-1225ye can be either a separate feed stream and/or a recycle stream (i.e., recycling HFO-1225ye derived from HFC-236ea as noted above). The HFC-245eb is again separated from the intermediate product stream and fed into a dehydrofluorination reactor to form a final product stream comprising HFO-1234yf. This HFO-1234yf is then separated from the final product stream and recovered as a purified product.

With any of the foregoing, the dehydrofluorination steps (e.g. 245eb→1234yf or 236ea→1225ye) occurs in the presence of at least one dehydrohalogenating agent, such as, but not limited to, potassium hydroxide (KOH), sodium hydroxide (NaOH), calcium hydroxide (Ca(OH)$_2$), lithium hydroxide (LiOH), magnesium hydroxide (Mg(OH)$_2$), calcium oxide (CaO), or combinations thereof. The amount of reagent used, or mole ratio of reagent to organic, will vary depending on the particular parameters present in each embodiment as discussed above, or otherwise herein. In certain embodiments, the mol ratio of dehydrohalogenating agent to organic feeds (e.g. HFC-245eb and/or HFC-236ea) is from less than 1 to 3, preferably 1-1.5.

Dehydrohalogenation can be performed in any suitable reaction vessel or reactor. In certain non-limiting embodiments, the reactor includes one or a series of Continuously Stirred Tank Reactors (CSTR), where organic (e.g. HFC-236ea and/or HFC-245eb) and dehydrohalogenating agent are fed continuously into the reactor. From the reaction product stream, a stream of spent dehydrohalogenating agent may be withdrawn and purified on a continuous or intermittent basis.

In certain embodiments, the stream of spent dehydrohalogenating agent further includes one or more dissolved organics, such as, but not limited to HFC-236ea and/or HFC-245eb. The spent dehydrohalogenating agent may be purified from such organics using one or more known separation methods. Such methods include, but are not limited to, distillation and/or phase separation. The resulting dehydrohalogenating agent can then be, optionally, concentrated and recycled back to the dehydrohalogenation reaction independently, or otherwise with one or more organics, as provided herein.

In further embodiments, the product stream also includes a salt by-product of the dehydrohalogenation reaction. The salt by-product may be isolated from the product stream using known techniques and converted back to the dehydrohalogenating agent using known methods. It may then be recycled to the dehydrohalogenation reaction independently or with one or more of the organics provided herein. By way of non-limiting example, one such salt by-product may be potassium fluoride (KF), which is formed when potassium hydroxide is used as the dehydrohalogenation agent. KF may be converted to KOH by treatment with Ca(OH)$_2$ (calcium hydroxide) according to the reaction:

$$2KF + Ca(OH)_2 \rightarrow 2KOH + CaF_2$$

The resulting KOH can be, optionally, concentrated and recycled back to the dehydrohalogenation reaction independently, or otherwise with one or more organics, as provided herein.

Additional embodiments and advantages of the instant invention will be readily apparent to one of skill in the art based on the disclosure provided herein.

BRIEF DESCRIPTION OF THE DRAWINGS

FIG. 1 is a process flow diagram showing the production of fluoroolefins according to an embodiment of the invention.

FIG. 2 is a process flow diagram showing the hydrogenation unit operation according to an embodiment of the invention.

FIG. 3 is a process flow diagram showing the hydrogenation unit operation according to another embodiment of the invention.

DETAILED DESCRIPTION OF THE INVENTION

Figure 4:
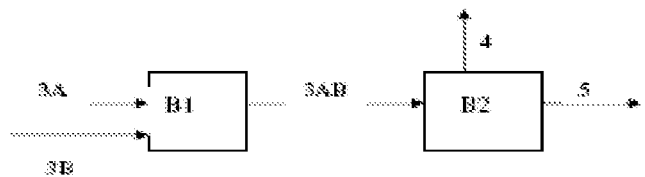
FIG. 4 is a process flow diagram showing the first separation unit operation according to an embodiment of the invention.

The instant invention relates, at least in part, to a method increasing the cost efficiency for dehydrohalogenation production of a fluorinated olefin by recovering and recycling spent dehydrohalogenation agent. In one aspect, the present invention relates to dehydrohalogenating a fluorinated alkane (e.g. pentafluoropropane and/or hexafluoropropane) in the presence of a dehydrohalogenating agent to produce a fluorinated olefin (e.g. tetrafluoropropenes and/or pentafluoropropenes). Removal of spent dehydrohalogenating agent from the reactor reduces design and operation costs and recycling the spent and/or regenerated dehydrohalogenating agent leads to improved efficiency. In certain embodiments, the dehydrohalogenating agent may include, but is not limited to, potassium hydroxide (KOH), sodium hydroxide (NaOH), calcium hydroxide (Ca(OH)$_2$), lithium hydroxide (LiOH), magnesium hydroxide (MgOH), calcium oxide (CaO) or combinations thereof. In further embodiments, the dehydrohalogenating agent is potassium hydroxide (KOH).

In certain embodiments, the fluorinated olefins of the present invention include one or more C3 to C6 fluoroalkenes, preferably compounds having a formula as follows:

$$X^1CF_zR_{3-z}$$

where $X^1$ is a C2, C3, C4, or C5 unsaturated, substituted or unsubstituted, alkyl radical, each R is independently Cl, F, Br, I or H, and z is 1 to 3. Highly preferred among such compounds are propenes and butenes having from 3 to 5 fluorine substituents, and among these tetrafluoropropenes (HFO-1234) and pentafluoropropenes (HFO-1225) are especially preferred.

In one embodiment, the processes for producing the fluorinated olefins of the present invention include reacting a fluorinated olefin starting material with a degree of halogen substitution of N+1 having substantially the same number of carbon atoms as the fluorinated olefin(s) to be synthesized with a degree of halogen substitution of N. The fluorinated olefin starting material preferably, though not exclusively, has a degree of fluorine substitution of N+1 and is exposed to reaction conditions effective to produce a reaction product containing one or more fluorinated alkanes having the same number of carbons atoms as the final olefin. This olefin conversion step includes a reaction that is sometimes referred to herein for convenience, but not necessarily by way of limitation, as a reduction or hydrogenation step. The resulting fluorinated alkane is then converted to a fluorinated olefin having a degree of fluorine substitution of N. This alkane conversion step comprises a reaction that is sometimes referred to herein for convenience, but not necessarily by way of limitation, as a dehydrohalogenation reaction or more particularly in certain embodiments as a dehydrofluorination or dehydrochlorination reaction.

Based on the foregoing, in one aspect of the present invention, the processes for producing a fluoroolefin includes the following steps:

(a) hydrogenating a compound of formula (I):

$$(CX_nY_{3-n})(CR^1{}_aR^2{}_b)_zCX=CH_mX_{2-m} \qquad (I)$$

under conditions effective to form at least one fluorinated alkane of formula (II)

$$(CX_nY_{3-n})(CR^1{}_aR^2{}_b)_zCHXCH_{m+1}X_{2-m} \quad (II)$$

where:
each X is independently Cl, F, I or Br, provided that at least two Xs are F;
each Y is independently H, Cl, F, I or Br;
each $R^1$ is independently H, Cl, F, I, Br or unsubstituted or halogen substituted methyl or ethyl radical;
each $R_2$ is independently H, Cl, F, I, Br or unsubstituted or halogen substituted methyl or ethyl radical;
n is 1, 2 or 3;
a and b are each 0, 1 or 2, provided that a+b=2;
m is 0, 1 or 2; and
z is 0, 1, 2 or 3; and (b) dehydrohalogenating the compound of formula (II) under conditions effective to produce a fluoroolefin with a lower degree of fluorine substitution than the compound of formula (I), preferably to produce a compound of formula (III):

$$(CX_nY_{3-n})(CR^1{}_aR^2{}_b)_zCX=CH_{m+1}X_{1-m} \quad (III)$$

where each n is the same value as in formula (I) and m is 0 or 1.

In further non-limiting embodiments, the reactant of formula (I) may include a three carbon olefin of formula (IA) wherein z is 0, namely $$CX_nY_{3-n}CX=CH_mX_{2-m} \quad (IA)$$

to produce a three carbon alkane of formula (IIA) as follows:

$$(CX_nY_{3-n})CHXCH_{m+1}X_{2-m} \quad (IIA)$$

where X, Y, n, and m are all as indicated above, which compound is then dehydrohalogenated to form a compound of formula (IIIA)

$$(CX_nY_{3-n})CX=CH_{m+1}X_{1-m} \quad (IIIA)$$

where n is the same value as in formula (IA) and m is 0 or 1.

In even further embodiments, the instant invention provides a saturated terminal carbon of the compounds of formulas (I) or (IA) that is fully substituted with fluorine (for example, n on the saturated terminal carbon is 3 and each X on that carbon is F). In such embodiments, the compound of Formula (I) or (IA) is preferably a fluoropropene having from three to six fluorine substituents, and potentially other halogen substituents, including for example hexafluoropropene (that is, Z is 0, n is 3, m is 0, and all X are F) or pentafluoropropene (that is, Z is 0, n is 3, m is 1, and all X are F). The resulting compound of formula (II) or (IIA) is selected from the group consisting of, one or more of the following fluorinated alkanes: pentafluoropropane (HFC-245) and hexafluoropropane (HFC-236), including all isomers of each of these, but preferably 1,1,1,2,3-pentafluoropropane (HFC-245eb), 1,1,1,2,3,3-hexafluoropropane (HFC-236ea) and combinations of these. In certain preferred embodiments the fluorinated alkane produced by the conversion step has a degree of fluorine substitution of N+1.

In any of the foregoing reactions, the step wherein the olefin is converted to an alkane is carried out under conditions effective to provide a formula (I) conversion of at least about 40%, more preferably at least about 55%, and even more preferably at least about 70%. In certain preferred embodiments the conversion is at least about 90%, and more preferably about 99%. Further in certain preferred embodiments, the conversion of the compound of formula (I) or (IA) to produce a compound of formula (II) is conducted under conditions effective to provide a formula (II) or (IIA) selectivity of at least about 60%, more preferably at least about 80%, and more preferably at least about 90%, and even more preferably about 100%.

In any of the foregoing reactions, the step wherein the alkane is converted to a fluorinated olefin having a degree of fluorination of N is carried out under conditions effective to provide a formula (II) conversion of at least about 40%, more preferably at least about 55%, and even more preferably at least about 70%. In certain preferred embodiments the conversion is at least about 90%, and more preferably about 95%. Further in certain preferred embodiments, the conversion of the compound of formula (II) to produce a compound of formula (III) is conducted under conditions effective to provide a formula (III) selectivity of at least about 60%, more preferably at least about 80%, and more preferably at least about 90%, and even more preferably about 98%.

The Hydrogenation Step

Although it is contemplated that the hydrogenation or reduction step may be conducted in batch operation, it is preferred that the hydrogenation reaction is carried out as a substantially continuous operation. While it is contemplated that the hydrogenation reaction may be conducted in a single reaction vessel, this reaction step may comprise two or more reactors or reaction stages in parallel, in series, or both, or any combination of reactor designs. In addition, it is contemplated that the reaction step may include one or more feed preheating steps or stages, depending on the particulars of each application.

While it is possible that the reaction may involve in certain embodiments a liquid phase reaction, it is contemplated that in certain embodiments the hydrogenation reaction comprises at least one vapor phase reaction stage.

In one embodiment of the present invention, as illustrated in FIG. 2, the hydrogenation step comprises a reaction step A having associated therewith at least a first flow path or feed stream 1A, at least a second flow path or feed stream 1B and at least a third flow path or feed stream 2, with each flow path being independently operable. In such embodiments, it is preferred that the first flow path or feed stream 1A comprises HFP and preferably substantially all of the HFP being fed to the reaction step A, the second path or feed stream 1B comprises HFO-1225ye, and preferably substantially all of the HFO-1225ye being fed to the reaction step A (it being recognized that the feed stream 1B in many embodiments will have a substantially zero flow and that in other embodiments this feed stream 1B may in fact be a recycle stream from subsequent operations in the process). The feed stream 2 comprises the hydrogenation or reducing agent, preferably $H_2$, for the reaction step A. Flow path or stream 4 is at path for allowing introduction of a recycle stream into the reaction step. In some embodiments, the actual flow of recycle stream 4 is zero, but in preferred embodiments, the recycle stream comprises a relatively low temperature stream comprising a portion of the reaction product stream 3A after it has been cooled and/or separated, the content of recycle stream 4, when present, preferably being relatively rich in HFC-236ea, HFC-245eb, or a combination of these.

In another preferred embodiment of the present invention as illustrated in FIG. 3, the hydrogenation step comprises at least a first reaction step A1 and a second reaction step A2. In one embodiment, the first reaction step A1, which may comprise one or more reaction stages in parallel or in series or a combination of parallel or series, having associated therewith at least a first flow path or feed stream 1A and at least a second flow path or feed stream 2A, with each flow path being independently operable. In such embodiments, it is preferred that the first flow path or feed stream 1A comprises HFP and preferably substantially all of the HFP being fed to the reaction step A, the second path or feed stream 2A comprises the hydrogenation agent, preferably $H_2$, for the reaction step A.

Flow path or stream 4A is at path for allowing introduction of a recycle stream into the reaction step. In some embodiments, the actual flow of recycle stream 4A is substantially zero, but in preferred embodiments, the recycle stream comprises a relatively low temperature stream comprising a portion of the reaction product stream 3A after it has been cooled and/or separated, the content of recycle stream 4, when present, preferably being relatively rich in HFC-236ea, HFC-245eb, or a combination of these.

In connection with the reaction stage converting HFP in the hydrogenation reactor at step A1, it is preferred in certain embodiments to use a trickle bed reactor. It is contemplated that the reaction is such case proceeds as follows:

$$CF_3CF{=}CF_2 + H_2 \rightarrow CF_3CHFCF_2H \text{ (HFC-236ea)}.$$

A major side reaction of this process yields HFC-245eb and HF. It is believed that 245eb is formed from 236ea by hydrodefluorination and/or by dehydrofluorination followed by reduction:

$$HFC\text{-}236ea + H_2 \rightarrow HFC\text{-}245eb + HF.$$

The second reaction step A2, may comprise one or more reaction stages in parallel or in series or a combination of parallel or series, having associated therewith at least a first flow path or feed stream 1B and at least a second flow path or feed stream 2B, with each flow path being independently operable. In such embodiments, it is preferred that the first flow path or feed stream 1B, when present, comprises HFO-1225ye, and preferably substantially all of the HFO-1225ye being fed to the reaction step A. The second path or feed stream 2B comprises the hydrogenation agent, preferably $H_2$, for the reaction step A2. Flow path or stream 4B is at path for allowing introduction of a recycle stream into the reaction step. In some embodiments, the actual flow of recycle stream 4B is zero, but in preferred embodiments, the recycle stream comprises a relatively low temperature stream comprising a portion of the reaction product stream 3A and/or 3B after it has been cooled and separated, the content of recycle stream 4B, when present, preferably being relatively rich in HFC-236ea, HFC-245eb, or a combination of these. Flow path or stream 10 is at path for allowing introduction of a second recycle stream into the reaction step, which in preferred embodiments comprises at least a portion of the reaction product stream 6 after being processed to comprise a stream relatively rich in HFO-1225ye.

In connection with the reaction stage converting HFO-1225ye in the hydrogenation reactor at step A2, it is preferred in certain embodiments to use a trickle bed reactor. It is contemplated that the reaction is such case proceeds as follows:

$$CF_3CF{=}CFH \text{ (liq)} + H_2 \text{ (gas)} \rightarrow CF_3CHFCFH_2 \text{ (HFC-245eb-gas)}$$

A major side reaction is contemplated to be:

$$HFC\text{-}245eb + H_2 \rightarrow CF_3CHFCH_3 \text{ (HFC-254)} + HF$$

Preferably, the hydrogenation reaction conditions are controlled in the reaction in order to achieve the desired conversion and/or selectivity in accordance with the present invention. As used herein, the term "reaction conditions" is intended to include the singular and means control of any one or more processing parameters, including possibly using or not using a reaction vessel or stage, which can be modified by the operator of the reaction to produce the conversion and/or selectivity of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein. The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

Those skilled in the art will be readily able to select the type of catalyst(s) used for the hydrogenation step of the present invention in view of the teachings contained herein. For example, it is preferred in certain embodiments that at least one, but preferably all, reaction stages utilize palladium catalyst, preferably 1% palladium on carbon, either alone or in combination with other catalysts. In this regard one or more of the hydrogenation catalysts disclosed in U.S. Pat. No. 5,679,875, which is incorporated herein by reference, may be used for one or more of the reaction stages in accordance with the present invention. In certain preferred embodiments, the catalyst preferably comprises palladium supported on carbon, such as a carbon mesh.

Thus, certain embodiments of the present methods comprise bringing a fluorinated olefin in accordance with formula I and a hydrogenation agent, such as $H_2$, into contact with a first amount of catalyst in at least a first reaction stage to produce a reaction stream comprising hydrofluorocarbon(s), unreacted fluorinated olefin and hydrogen. In certain preferred embodiments the hydrogenation step is followed by a preferred separation step as described below. While it is contemplated that a wide variety of hydrogenation reaction temperatures may be used, depending on relevant factors such as the catalyst being used and the most desired reaction product, it is generally preferred that the reaction temperature for the hydrogenation step is from about 50° C. to about 150° C., preferably about from 75° C. to about 115° C., and even more preferably from about 90° C. to about 100° C.

In general, it is also contemplated that a wide variety of reaction pressures may be used, depending again on relevant factors such as the specific catalyst being used and the most desired reaction product. The reaction pressure can be, for example, from about 100 psig to about 300 psig, preferably about from 150 psig to about 250 psig, and even more preferably about 200 psig.

Applicants have found, without being bound by or to any particular theory, that the use of a cooled recycle stream 4, 4A, or 4B in the hydrogenation reaction allows the feed materials to serve as a means for removing heat from the hydrogenation reaction. Since the reduction or hydrogenation reaction of the present invention is generally exothermic, and usually substantially exothermic, the use of such a recycle material has the effect in preferred embodiments of maintaining the reactor temperature below that which would exist if the recycle were not used, assuming all other process conditions were maintained the same.

It is contemplated that the amount of hydrogen used may vary widely. In preferred embodiments, the hydrogen is feed to the reaction step as a gas in a $H_2$:olefin feed ratio of from about 1:1 to about 2:1, and even more preferably ratio of from about 1:1 to about 1.5:1, and even more preferably about 1.3:1.

The Hydrogenation Reaction Effluent Separation

In certain preferred embodiments, the present invention also includes the step of cooling at least a portion reactor product stream (3, 3A, 3B) to remove at least a portion of the heat of reaction. In many preferred embodiments, this cooling step is included as part of the preferred aspects of the separation step B, which are described in connection with FIGS. 4, 5 and 6 below. Preferably the ratio of cooled recycled reaction product to fresh feed is about 12:1, with the temperature of the recycle stream preferably being at about 50° C. to about 100° C., and even more preferably about 70° C. In addition, in order to help remove heat of reaction, it is preferred in certain embodiments to introduce the fresh feeds and/or the recycle feeds to the reaction in the liquid phase and allowing the heat of reaction to evaporate the liquid feed and/or the reaction products and withdrawing the reaction products in the gas phase.

With reference now to FIG. 4, the reaction product streams 3A and 3B are directed to a separation step B, which comprises in the embodiment of FIG. 4 a cooling step B1 which produces one or more cooled reaction product streams 3AB, which in turn are fed to one or more separation stages B2. It is contemplated that those skilled in the art will be able to devise without undue experimentation many means and mechanisms for attaining such cooling in view of the teachings contained herein and all such means and mechanisms are with the scope of the present invention. The preferred separation step B2 preferably includes at least a first separation step which produces a first stream 4 relatively rich in unreacted hydrogen, fluorinated alkane, such as HFC-236ea and/or HFC-245eb, or a combination of these, which may be recycled, with or without further processing, to the reaction step A. A second stream 5, which is relatively rich in the fluorinated alkane, such as HFC-236ea and/or HFC-245eb, is also produced from the separation step B2.

Figure 4A:
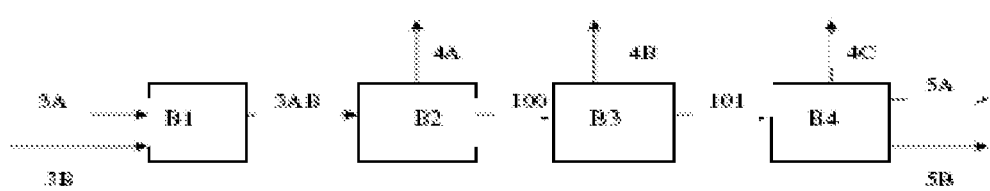

In one preferred embodiment shown in FIG. 4A, the separation step comprises, in addition to the cooling step B1 and the separation step B2 which produces at least a first cooled stream 4A containing a portion of the reaction product, which is preferably recycled to the reaction step A, and a crude product stream 100 which is fed to a further separation step B3 in which a substantial portion of excess hydrogen in the stream 100 is purged from the stream and sent for disposal or further processing in stream 4B. The stream 101 from the separation step B3 is then feed to a further separation step B4 where unwanted by-products are removed in stream 4C and one or more product streams 5A and 5B are produced. In preferred embodiments, stream 5A is relatively rich in a first fluorinated alkane, preferably HFC-236ea, and a second stream 5B rich in a second fluorinated alkane, preferably HFC-245eb.

Figure 5:
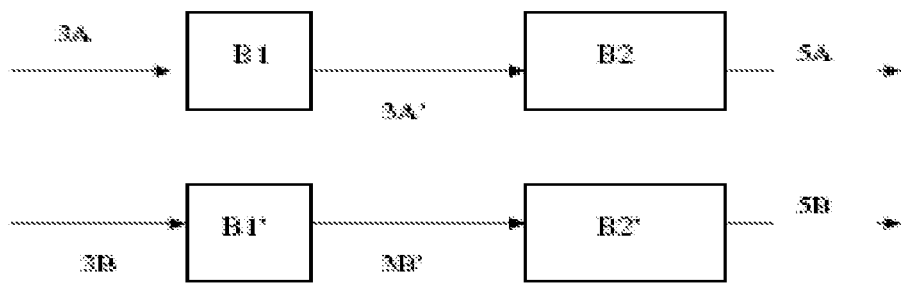
FIG. 5 is a process flow diagram showing the first separation unit operation according to another embodiment of the invention.

In another embodiment described with reference now to FIG. 5, the reaction product streams 3A and 3B are each directed to a separate separation steps, which comprise separate cooling steps B1 and B1', each of which produces one or more cooled reaction product streams 3A' and 3B', which in turn are fed to separate separation stages B2 and B2' to produce a first stream 5A relatively rich in a first of the fluorinated alkane products, such as HFC-236ea when the feed stream 3A is rich in HFP, and a second reaction product stream 5B relatively rich in a second of the fluorinated alkane products, such as HFC-245eb when the feed stream 3B is rich in HFO-1225ye. A stream 4 (not shown) as described above in connection with FIG. 4 may also be removed from each of the steps B2 and B2'. In addition, the particular embodiments shown and described in FIG. 4A may also be adapted for use in connection with one or both the separation steps B and B' shown in FIG. 5.

Dehydrohalogenation

The dehydrofluorination step can be carried out in a liquid phase in the presence of a dehydrohalogenation agent (e.g. caustic solution) or a gas phase in the presence of a dehydrofluorination catalyst. It is contemplated that the reaction may be carried out batchwise, continuously or a combination thereof.

In one embodiment the converting step involves a reaction in which HFC-245eb and/or HFC-236ea is contacted with a dehydrohalogenating agent such as KOH, NaOH, $Ca(OH)_2$, LiOH, $Mg(OH)_2$, CaO, and combinations thereof to form the fluorinated olefin. By way of example, if KOH is used, such a reaction may be described by way of illustration, but not necessarily by way of limitation, by the following reaction equations (1) and (2):

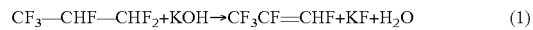

$$CF_3-CHF-CHF_2+KOH \rightarrow CF_3CF=CHF+KF+H_2O \quad (1)$$

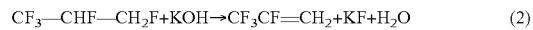

$$CF_3-CHF-CH_2F+KOH \rightarrow CF_3CF=CH_2+KF+H_2O \quad (2)$$

The dehydrohalogenating agent may be provided as a caustic aqueous solution comprising from about 2% to about 100%, more preferably from about 10% to about 50%, and even more preferably from about 10% to about 30% by weight of dehydrohalogenating agent. In further embodiments, the caustic solution, and preferably the dehydrohalogenating agent solution, is brought to a temperature of from about 20° C. to about 100° C., more preferably from about 20° C. to about 90° C., and most preferably from about 20° C. to about 70° C. The reaction pressure in such embodiments may vary, depending on particular processing parameters of each application. In certain embodiments, the reaction pressure ranges from atmospheric pressure, super-atmospheric pressure or under vacuum. The vacuum pressure, when used, in certain embodiments ranges from about 5 torr to about 760 torr.

It is contemplated that the amount of dehydrohalogenation agent (or reagent) used, or mole ratio of reagent to organic, will vary depending on the particular parameters present in each embodiment. In certain embodiments, the mol ratio of dehydrohalogenating agent to organic feeds (e.g. HFC-245eb and/or HFC-236ea) is from less than 1 to 3, preferably 1-1.5. In further embodiments, the contact time, which is expressed as the ratio of the volume of the reagent (ml) to the total feed flow (ml/sec) is from about 0.1 seconds to about 1000 seconds, and preferably from about 2 seconds to about 120 seconds.

The dehydrohalogenation reactions can be accomplished using any suitable vessel or reactor. Such vessels or reactors should be constructed from materials which are resistant to corrosion, such as stainless steel, nickel and its alloys, including Hastelloy, Inconel, Incoloy, and Monel. In certain embodiments, this reaction is performed using one or a series of Continuously Stirred Tank Reactors (CSTR). In this type of reactor, organic feed (e.g. HFC-236ea and/or HFC-245eb) and dehydrohalogenating agent would be fed continuously into the reactor and the resulting product stream formed would be fed into a condenser or distillation column for separation of 1225ye and/or 1234yf from and un-reacted 236ea and/or 245eb, as well as other by-products of the reaction.

In certain embodiments, spent dehydrohalogenating agent is removed from the product stream either periodically or continuously and is recycled back to the reactor for reuse. As noted previously, Applicants have discovered that, during continuous processing the reaction proceeds until either the organic reactants (e.g. HFC-236ea and/or HFC-245eb) or dehydrohalogenating agent is consumed. This increases costs of productivity because the reactor must be dismantled upon completion of the reaction to remove the salt and/or salt solutions. By recycling the dehydrohalogenating agent and by-product salts, however, such costs may be reduced and the system made more efficient.

Spent dehydrohalogenating agent and by-product salts (e.g. metal fluoride salts) may be withdrawn from the reactor by a product stream either continuously or intermittently using one or more known separation techniques. To this end, spent dehydrohalogenating agent separation may occur using any known compound separation techniques, such, but not limited to, distillation, phase separation, etc. In certain embodiments, withdrawal of spent dehydrohalogenating agent is especially beneficial for component separation as it allows for facile separation of organic and dehydrohalogenating agent. This in turn leads to lower cost associated with design and operation of complicated and highly specialized separation equipment.

The product stream containing spent dehydrohalogenating agent typically carries with it some dissolved organic (e.g. HFC-236ea and/or HFC-245eb). By stopping the stirrer and then removing spent dehydrohalogenating agent during the time agitation is stopped, separation of dehydrohalogenating agent and such organic can be facilitated. Spent dehydrohalogenating agent and dissolved organic would be taken into a container where additional separation of dehydrohalogenating agent and organic can be accomplished using one or more of the foregoing separation techniques. In one non-limiting embodiment, for example, KOH is separation by distillation, i.e. by heating organic just above boiling point of 236ea and/or 245eb, thus fractionating the organic from the spent KOH. Alternatively, one can use phase separator to separate between the two phases. The organic free KOH isolate can be immediately recycled to the reactor or can be concentrated and the concentrated solution can be returned to reactor.

The by-product salt can also be isolated and converted back to the dehydrohalogenating agent used known methods. When KOH is used as the dehydrohalogenating agent, for example, KF is formed as a by-product salt. Such salt may be converted back to KOH and recycled back to the dehydrohalogenation reaction. For example, $Ca(OH)_2$ can be used for KF conversion according to reaction below.

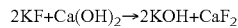

$CaF_2$ will precipitate from the foregoing reaction while KOH is isolated and recycled back to reactor. Recycling of spent dehydrohalogenating agent leads to better efficiency of the reagent use. Moreover, the use of recycling of the by-product salt reduces dehydrohalogenating agent use, reduces costs of reagents and costs associated with disposal of the salt, and/or purchase of new raw material.

Figure 6:
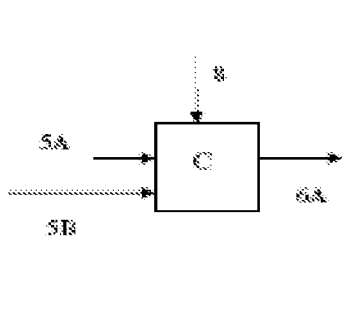
FIG. 6 is a process flow diagram showing the dehydrofluorination unit operation according to an embodiment of the invention.

In one embodiment of the present invention, and referring to FIG. 6, the dehydrohalogenation step comprises a reaction step C having associated therewith at least a first flow path or feed stream 5A, at least a second flow path or feed stream 5B and at least a third flow path or feed stream 8, with each flow path being independently operable. In such embodiments, it is preferred that the first flow path or feed stream 5A comprises HFO-236ea and preferably substantially all of the HFO-236ea being fed to the reaction step C, the second path or feed stream 5B comprises HFC-245eb, and preferably substantially all of the HFO-245eb being fed to the reaction step C (it being recognized that the feed stream 5B in many embodiments will have a substantially zero flow). Flow path or stream 8 is at path for allowing introduction of a recycle stream into the reaction step. In some embodiments, the actual flow of recycle stream 8 is zero, but in preferred embodiments, the recycle stream comprises a relatively low temperature stream comprising a portion of the reaction product stream 6A after it has been cooled and/or separated. The content of recycle stream 8, when present, may include unreacted organic (e.g. HFC-236ea, HFC-245eb) and spent dehydrohalogenating agent. Each may be purified or recovered, as provided herein and recycled.

Figure 7:
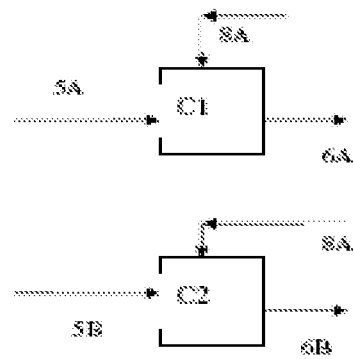
FIG. 7 is a process flow diagram showing the dehydrofluorination unit operation according to another embodiment of the invention.

In another preferred embodiment of the present invention as illustrated in FIG. 7, the dehydrohalogenation step comprises at least a first reaction step C1 and a second reaction step C2. The first reaction step C1, which may comprise one or more reaction stages in parallel or in series or a combination of parallel or series, having associated therewith at least a first flow path or feed stream 5A and at least a second flow path or feed stream 8A, with each flow path being independently operable. The second reaction step C2, which may comprise one or more reaction stages in parallel or in series or a combination of parallel or series, having associated therewith at least a first flow path or feed stream 5B and at least a second flow path or feed stream 8B, with each flow path being independently operable. In such embodiments, it is preferred that the first flow path or feed stream 5A comprises HFO-236ea and preferably substantially all of the HFO-236ea being fed to the reaction step C, the second path or feed stream 5B comprises, when present, HFO-245eb and preferably substantially all of the HFO-245eb being fed to the reaction step C. Flow path or streams 8A and 8B are flow paths for allowing introduction of a recycle stream comprising at least a portion of unreacted feed back or recycled dehydrohalogenating agent, as defined herein. In some embodiments, the actual flow of recycle streams 8A and 8B are substantially zero, but in preferred embodiments, the recycle streams comprises relatively low temperature streams comprising a portion of the reaction product streams 6A and 6B after they have been cooled and separated.

Preferably, the reaction conditions are controlled in the reaction in order to achieve the desired conversion and/or selectivity in accordance with the present invention. As used herein, the term "reaction conditions" is intended to include the singular and means control of any one or more processing parameters, including possibly using or not using a reaction vessel or stage, which can be modified by the operator of the reaction to produce the conversion and/or selectivity of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein. The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

The resulting products may be isolated from the product stream using one or more methods known in the art and purified accordingly.

EXAMPLES

The following examples are provided for the purpose of illustrating the present invention but without limiting the scope thereof.

Example 1

A CSTR (Continuously Stirred Tank Reactor) was used to convert 245eb to 1234yf. The reactor was designed and operated in such a way that the end of the dip tube was in the middle of KOH phase. After the startup, organic and fresh KOH were constantly fed in. Organic out (the overhead portion) was constantly taken out. In a typical cycle organic and KOH flow in and overhead is taken out for 30 min. Flowrates were 5 and 12 ml/min, respectively. The mixture is stirred during this period of time. Then stirrer is stopped for 10 min, while feeds still go in. While stirrer is off, after 10 min, applicable valves for the spent KOH to go out were open. Between 500 and 550 g was taken out every 40 min.

Experiment was carried out for 7 hours. Temperature was 48° C. Pressure was 45 psig. GC area percent of the organic feed was ~97% of 245eb, the rest being most probably 254. The flowrates translate to mol ratio of KOH to G-245eb of 1, or slightly above 1. Theoretical residence time was 100 min.

Scrubber Product Collection Cylinder (SPCC) was used to collect spent KOH and the portion of organic that was carried out with spent KOH. Organic was trapped in methylene chloride which was previously added to SPCC. The volume of methylene chloride inside the SPCC was 15% of the total volume of liquid in SPCC. Product and un-reacted organic was collected in a Product Collection Cylinder (PCC) that was held in dry ice. Vapor samples were taken once per hour while liquid samples were taken at much longer intervals.

Overall mass balance was 94% for organic. Average conversion was 48%. Selectivity to 1234yf was 73%.

Example 2

The second experiment was carried out in the same fashion as the experiment 1, except that pressure and temperature were 48 psig and 47° C. Experiment lasted 6 hours and overall conversion was 69%. Selectivity to 1234yf was 75%.

Example 3

Reactor was loaded with 807 ml of organic. The feed was analyzed by GC to reveal Area % for 236ea as 97.70%. There was no 1234yf in this feed, while the percentage of 1225ye was 0.03. After loading the reactor with organic, 1641 ml of 25% KOH was added. Therefore mol ratio of KOH to 236ea was 1.23.

The flowrates of 236ea and KOH were 2 and 4 ml/min. Pressure was 35-45 psig. Reactor temperature was 42-45° C.

Spent KOH was taken out of reactor periodically (it was fed continuously as was organic; overhead product was taken out continuously, i.e. semi-continuous operation). In this semi-continuous mode KOH and organics flowed into stirred reactor for 50 min. Then the stirrer was stopped for 10 min while reactants were still going in. Afterwards 290-300 g of spent KOH was taken out. Then stirrer was started as was the clock for 50 min time period.

Spent KOH was collected in Scrubber Product Collection Cylinder (SPCC). SPCC was pre-filled with methylene chloride (the target was to have 15-20 wt % of methylene chloride in the final spent KOH-methylene chloride solution). Analysis of methylene chloride layer revealed that ~70 GC area % was 236ea. There was small amount of 1225ye (~2%) while the rest were unidentified heavies. In order to confirm that all organic was extracted with methylene chloride, part KOH was added to part MeCl$_2$ (i.e. 1:1). GC analysis revealed that amount of organic was negligible.

Overall mass balance was 88.67%. Residence time was 200 min. The conversion was ~50%. Selectivity to 1225ye was 63%. The reaction was carried out for the total of 97 hours.

What is claimed is:
1. A method for producing at least one fluorinated olefin comprising:
   a. hydrogenating a starting material stream comprising at least one alkene according to Formula (I):

$$(CX_nY_{3-n})(CR^1{}_aR^2{}_b)_zCX\!\!=\!\!CH_mX_{2-m} \tag{I}$$

by contacting said starting material with a reducing agent to produce an intermediate product stream comprising at least one alkane according to Formula (II):

$$(CX_nY_{3-n})(CR^1{}_aR^2{}_b)_zCHXCH_{m+1}X_{2-m} \tag{II}$$

where:
   each X is independently Cl, F, I or Br, provided that at least two Xs are F;
   each Y is independently H, Cl, F, I or Br;
   each $R^1$ is independently H, Cl, F, I, Br or unsubstituted or halogen substituted methyl or ethyl radical;
   each $R_2$ is independently H, Cl, F, I, Br or unsubstituted or halogen substituted methyl or ethyl radical;
   n is 1, 2 or 3;
   a and b are each 0, 1 or 2, provided that a+b=2;
   m is 0, 1 or 2; and
   z is 0, 1, 2 or 3;
   b. optionally, separating said intermediate product stream into a plurality of intermediate product streams, said plurality of intermediate product streams comprising two or more streams selected from the group consisting of a first stream rich in at least a first alkane according to Formula II, a seconds stream rich in at least a second alkane according to Formula II, and an alkane recycle stream;
   c. dehydrofluorinating, in the presence of a dehydrohalogenating agent, at least a portion of said intermediate process stream from step (a) or said plurality of intermediate process streams of step (b) to produce an alkene product stream comprising 1,1,1,2,3-pentafluoropropene and at least one additional alkene having a lower degree of fluorine substitution compared to the degree of fluorination of the compound of formula (I); and d. withdrawing from a dehydrofluorinated product stream a product reaction stream comprising spent dehydrohalogenating agent; and e. recovering spent dehydrohalogenating agent.

2. The method of claim 1 wherein said additional alkene is a compound according to formula (III):

$$(CX_nY_{3-n})(CR^1{}_aR^2{}_b)_ZCX=CH_{m+1}X_{1-m} \qquad (III)$$

where each of X, Y, $R^1$, $R^2$, n, a, and b is the same value as in formula (I) and m is 0 or 1.

3. The method of claim 2 wherein Z is 0.

4. The method of claim 3 wherein m is 0 or 1.

5. The method of claim 4 wherein said n is 3.

6. The method of claim 5 wherein X is F.

7. The method of claim 1 wherein said reducing agent is $H_2$.

8. The method of claim 1 wherein said starting material stream comprises hexafluoropropylene and said additional alkene is 2,3,3,3-tetrafluoropropene.

9. The method of claim 1 wherein the dehydrohalogenating agent is selected from the group consisting of KOH, NaOH, $Ca(OH)_2$, LiOH, $Mg(OH)_2$, CaO, and combinations thereof.

10. A method for producing 2,3,3,3-tetrafluoropropene comprising:

a. hydrogenating a starting material stream comprising hexafluoropropylene by contacting said starting material stream with a reducing agent in a hydrogenation reactor to produce an intermediate stream comprising 1,1,1,2,3-pentafluoropropane or 1,1,1,2,3,3-hexafluoropropane;

b. dehydrofluorinating, in the presence of a dehydrohalogenating agent, said 1,1,1,2,3-pentafluoropropane or said 1,1,1,2,3,3-hexafluoropropane in a dehydrofluorination reactor to produce a product stream comprising 2,3,3,3-tetrafluoropropene or 1,2,3,3,3-pentafluoropropene;

c. withdrawing from the product stream a second product stream comprising spent dehydrohalogenating agent; and d. recovering spent dehydrohalogenating agent.

11. The method of claim 10 wherein the second product stream further comprises one or more dissolved organics.

12. The method of claim 11 wherein the dissolved organics are selected from the group consisting of 1,1,1,2,3,3-hexafluoropropane (HFC-236ea), 1,1,1,2,3-pentafluoropropane (HFC-245eb), and combinations thereof.

13. The method of claim 10 wherein the spent dehydrohalogenating agent is purified using at least one separation method.

14. The method of claim 13 wherein the separation method is selected from the group consisting of distillation or phase separation.

15. The method of claim 10 further comprising, optionally, concentrating the purified dehydrohalogenating agent and recycling it back to the dehydrohalogenation reaction.

16. The method of claim 10 wherein the reaction stream further comprises by-product salts of the dehydrohalogenating agent.

17. The method of claim 16 further comprising converting the by-product salts to the dehydrohalogenating agent.

18. The method of claim 16 wherein the dehydrohalogenating agent is KOH and the by-product salt is KF.

19. The method of claim 18 further comprising, optionally, concentrating the converted KOH and recycling it back to the dehydrohalogenation reaction.

20. The method of claim 18 further comprising converting KF to KOH in the presence of $Ca(OH)_2$.

21. A process for the manufacture of a fluoroolefin comprising:

(a) dehydrohalogenating a haloalkane in the presence of KOH to produce a haloalkene;

(b) withdrawing a reaction stream comprising spent KOH; and (c) recovering spent KOH.

22. The process of claim 21 wherein the haloalkane is comprised of a compound of formula (IIA):

$$(CX_nY_{3-n})CHXCH_{m+1}X_{2-m} \qquad (IIA)$$

wherein each X is independently selected from the group consisting of Cl, F, I and Br; each Y is independently selected from the group consisting of H, Cl, F, I, and Br; n is 1, 2, or 3; and m is 0, 1 or 2.

23. The process of claim 22 wherein the haloalkane is 1,1,1,2,3,3-hexafluoropropane (HFC-236ea) or 1,1,1,2,3-pentafluoropropane (HFC-245eb).

24. The process of claim 21 wherein the haloalkene is comprised of a compound of formula (IIIA):

$$(CX_nY_{3-n})CX=CH_{m+1}X_{1-m} \qquad (IIIA)$$

wherein each X is independently selected from the group consisting of Cl, F, I and Br; each Y is independently selected from the group consisting of H, Cl, F, I, and Br; n is 1, 2, or 3; and m is 0 or 1.

25. The process of claim 24 wherein the haloalkene is 2,3,3,3-tetrafluoropropene (HFO-1234yf) or 1,2,3,3,3-pentafluoropropene (HFO-1225ye).

26. The process of claim 21 wherein the dehydrohalogenation occurs using a continuously stirred tank reactor.

27. The process of claim 21 wherein the spent KOH is withdrawn from the reactor continuously or intermittently.

28. The process of claim 21 wherein the reaction stream further comprises a dissolved organics.

29. The process of claim 28 wherein the dissolved organics are selected from the group consisting of 1,1,1,2,3,3-hexafluoropropane (HFC-236ea) or 1,1,1,2,3-pentafluoropropane (HFC-245eb).

30. The process of claim 21 wherein the spent KOH is purified using at least one separation method.

31. The process of claim 30 wherein the separation method is selected from the group consisting of distillation or phase separation.

32. The process of claim 21 further comprising, optionally, concentrating the purified KOH and recycling it back to the dehydrohalogenation reaction.

33. The process of claim 21 wherein the reaction stream further comprises KF.

34. The process of claim 33 further comprising converting KF to KOH in the presence of $Ca(OH)_2$.

35. The process of claim 34 further comprising, optionally, concentrating the converted KOH and recycling it back to the dehydrohalogenation reaction.

36. A process for the manufacture of a fluoroolefin comprising:

(a) dehydrohalogenating 1,1,1,2,3,3-hexafluoropropane (HFC-236ea) or 1,1,1,2,3-pentafluoropropane (HFC-245eb) in the presence of KOH to produce 2,3,3,3-tetrafluoropropene (HFO-1234yf) or 1,2,3,3,3-pentafluoropropene (HFO-1225ye);

(b) withdrawing a reaction stream comprising spent KOH; and (c) recovering spent KOH.

37. The process of claim 36 wherein the dehydrohalogenation occurs using a continuously stirred tank reactor.

38. The process of claim 36 wherein the spent KOH is withdrawn from the reactor continuously or intermittently.

39. The process of claim 36 wherein the reaction stream further comprises a dissolved organics.

40. The process of claim 37 wherein the dissolved organics are selected from the group consisting of 1,1,1,2,3,3-hexafluoropropane (HFC-236ea) or 1,1,1,2,3-pentafluoropropane (HFC-245eb).

41. The process of claim 36 wherein the spent KOH is purified using at least one separation method.

42. The process of claim 41 wherein the separation method is selected from the group consisting of distillation or phase separation.

43. The process of claim 36 further comprising, optionally, concentrating the purified KOH and recycling it back to the dehydrohalogenation reaction.

44. The process of claim 36 wherein the reaction stream further comprises KF.

45. The process of claim 44 further comprising purifying KF from the reaction stream.

46. The process of claim 36 further comprising converting KF to KOH in the presence of $Ca(OH)_2$, optionally, concentrating the KOH and recycling it back to the dehydrohalogenation reaction.

* * * * *